United States Patent
Nyholm

(10) Patent No.: US 7,893,926 B2
(45) Date of Patent: Feb. 22, 2011

(54) CONTROL ARRANGEMENT FOR DENTAL DEVICE AND METHOD OF CONTROLLING DENTAL DEVICE

(75) Inventor: Kustaa Nyholm, Siuntio kk (FI)

(73) Assignee: Planmeca Oy, Helsinki (FI)

( * ) Notice: Subject to any disclaimer, the term of this patent is extended or adjusted under 35 U.S.C. 154(b) by 1090 days.

(21) Appl. No.: 10/550,240

(22) PCT Filed: Mar. 24, 2004

(86) PCT No.: PCT/FI2004/000164
§ 371 (c)(1),
(2), (4) Date: Sep. 23, 2005

(87) PCT Pub. No.: WO2004/084753
PCT Pub. Date: Oct. 7, 2004

(65) Prior Publication Data
US 2006/0209038 A1    Sep. 21, 2006

(30) Foreign Application Priority Data
Mar. 25, 2003    (FI) ................. 20030451

(51) Int. Cl.
*G06F 3/041*    (2006.01)

(52) U.S. Cl. .................. 345/173; 345/156; 433/80

(58) Field of Classification Search ......... 345/156–158, 345/173; 433/25, 29, 80, 98, 101
See application file for complete search history.

(56) References Cited

U.S. PATENT DOCUMENTS

| | | | |
|---|---|---|---|
| 4,670,738 A | 6/1987 | Weinblatt | |
| 5,300,926 A | 4/1994 | Stoeckl | |
| 5,430,266 A | 7/1995 | Austin, Jr. et al. | |
| 5,550,564 A | 8/1996 | Cragun | |
| 5,558,371 A * | 9/1996 | Lordo | 285/114 |
| 6,204,837 B1 * | 3/2001 | Smith | 345/157 |
| 6,626,668 B2 * | 9/2003 | Hubert et al. | 433/80 |
| 6,909,424 B2 * | 6/2005 | Liebenow et al. | 345/169 |
| 2001/0002725 A1 | 6/2001 | Pollet et al. | |
| 2001/0013855 A1 * | 8/2001 | Fricker et al. | 345/156 |
| 2002/0111701 A1 | 8/2002 | Borders | |
| 2003/0048259 A1 * | 3/2003 | Rowe | 345/173 |

FOREIGN PATENT DOCUMENTS

EP    1 010 404 A2    6/2000

* cited by examiner

*Primary Examiner*—Kimnhung Nguyen
(74) *Attorney, Agent, or Firm*—Cozen O'Connor

(57) ABSTRACT

A dental apparatus which comprises a dental device, a graphic display and a user interface connected functionally to one another, the user interface being arranged to be used in controlling functions of the dental device. The user interface is a touch pad and the graphic display comprises means for showing symbols describing control functions of the dental device and a cursor. The dental apparatus further comprises means for moving and controlling the cursor in response to a touch of a pointer means and its movement on the surface of the touch pad. A detachable and disinfectable film, which can be replaced by a new one after it has worn out, may be attached to the contact surface.

10 Claims, 1 Drawing Sheet

CONTROL ARRANGEMENT FOR DENTAL DEVICE AND METHOD OF CONTROLLING DENTAL DEVICE

FIELD OF THE INVENTION

The invention relates to controlling a dental device, in particular to a hygienic control arrangement for a dental device.

BACKGROUND OF THE INVENTION

In all medical treatments, such as odontological treatments, disinfection of treatment instruments and environment is of high importance. The purpose of disinfection is to kill microbes and thus to guarantee that the treatment environment and devices are safe for patients. Disinfection can be carried out as thermal disinfection, for example by boiling an instrument or by sterilizing it in autoclave, or as chemical disinfection, for example by wiping an instrument with a suitable disinfectant or by soaking it in a disinfectant solution. In disinfection, however, attention has to be paid to the material of the instrument. For example, not all plastic types can be disinfected chemically since their surfaces may absorb disinfectant. Furthermore, some materials, such as plastics, do not sustain high temperatures, either. Several sensitive instruments do not endure autoclaving.

Disinfection is, however, a necessary measure in connection with daily dental care. Mere disinfection of instruments does not, however, guarantee a hygienic environment for dental care, but the dental apparatuses and their controls should be designed and manufactured so that their surfaces can be easily disinfected or they include detachable parts that endure autoclaving.

Dental devices are typically controlled by means of a keyboard interface integrated into the device and a 'foot control'. The keyboard is mainly used for setting operating parameters for the instruments and for similar control functions, and the foot control is employed for controlling the instruments during operation.

Doctors generally use computers for processing patient information. Computers are typically controlled by a controller placed next to the treatment device, such as a mouse or keys. In connection with treatments, doctors touch a patient with their hands, and if a computer is used in between, this poses a hygiene risk since microbes, such as bacteria and viruses, may be transmitted from the controller to the patient through touch.

It is known that cleaning and disinfection of typical controllers, such as a mouse or keyboard, is difficult due to their shape and materials. From the controller, microbes may be transmitted from the controller further to patients through touch, which is particularly detrimental in connection with dental treatment since, when the skin or mucous membranes are broken, the system is particularly vulnerable to microbes, which may cause infections, for example. The control surface can naturally be covered by a disposable or disinfectable protective cover, such as a plastic bag intended for the purpose, but in this case, the use of the control is difficult and the replacement or disinfection of the protective cover is relatively troublesome.

BRIEF DESCRIPTION OF THE INVENTION

The object of the invention is to provide a dental apparatus which comprises a dental device that can be controlled hygienically by a controller so as to alleviate the above-mentioned problems. The object of the invention is achieved by a dental apparatus and a method which are characterized by what is stated in the independent claims.

The preferred embodiments of the invention are disclosed in the dependent claims.

The idea underlying the invention is that the dental apparatus comprises a dental device, a graphic display and a user interface connected functionally to one another. The user interface is arranged to be used for controlling functions of the dental device. The user interface is a touch pad and the graphic display comprises means for showing symbols describing the control functions of the dental device, such as icons, and a cursor. The dental apparatus further comprises means for moving and controlling the cursor in response to a touch of a pointer means, such as a pointer pen or finger, and its movement on the surface of the touch pad. Such a touch pad typically comprises a uniform and even contact surface, which is easy to wipe with disinfectant. According to a preferred embodiment of the invention, a functional connection is arranged between the touch pad and the graphic display through a computer. Furthermore, according to a preferred embodiment of the invention, the touch pad is arranged to control a computer functionally connected to the dental device. In addition, according to a preferred embodiment of the invention, the touch pad is arranged to control the dental device through the computer. According to a further preferred embodiment of the invention, a detachable and disinfectable or disposable film, which can be replaced by a new one after it has worn out, is arranged to be attached to the contact surface.

According to a preferred embodiment of the invention, the touch pad comprises a capacitive or a resistive contact surface. According to a preferred embodiment of the invention, the touch pad is arranged to produce control information for the dental device in response to the fact that the contact surface of the touch pad is pressed or something slides on it so that the material layers included in the touch pad touch one another at the point in question, thus interrupting the current flow in the electrode network included in the touch pad.

According to a preferred embodiment of the invention, the touch pad is integrated into the dental apparatus, or correspondingly, the touch pad is placed under the backrest of the patient chair included in the dental apparatus.

According to a preferred embodiment of the invention, the dental apparatus further comprises a computer, in which case the touch pad is arranged to produce control information for the dental device through the computer so that control information is modified on the basis of the patient information included in the computer.

The apparatus according to the invention provides considerable advantages. An advantage is that the controller surface is easy to clean and disinfect between treatments or even during a treatment. Thus the use of the dental device according to the invention is considerably more hygienic than that of prior art dental devices. A further advantage is that the user can operate the controller also when wearing protective gloves, which facilitates the controlling of the dental device during a treatment. In addition, an advantage is that the controller can be placed relatively freely with respect to the dental device, and thus the controller can be, for example, integrated into a surface of the dental device, such as the top of a instrument table. Thus the controller can also be placed ergonomically in a suitable place, considering the motion path of the controller user's hands during the operation, for example.

BRIEF DESCRIPTION OF THE FIGURES

In the following, the invention will be described in greater detail with reference to the accompanying drawings, in which.

DETAILED DESCRIPTION OF THE INVENTION

Figure 1:
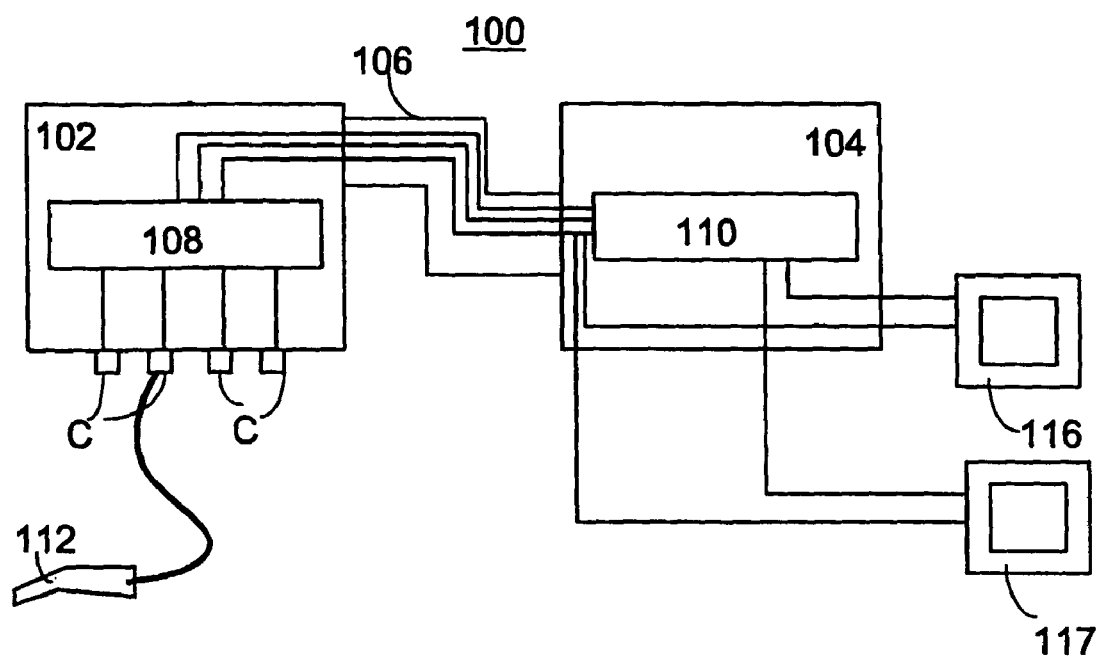
FIG. 1 is a block diagram illustrating a dental apparatus according to a preferred embodiment of the invention.

In the following, a preferred embodiment of the invention will be described referring to FIG. 1, which illustrates, as a block diagram, a dental apparatus 100, which includes a dental device and a control device connected functionally to it. In this application, the dental device refers to a device to which one or more instruments used in dental treatment can be attached. The dental device is generally arranged to feed power, water and/or compressed air into the instruments. The dental device typically comprises an instrument table 102, a frame part 104 and a cable conduit 106 connecting them. The instrument table 102 comprises an electronics unit 108, which is arranged to perform the functions needed to control the dental instruments. The frame part 104 comprises an electronics unit 110 of its own. The instruments 112 are attached to the instrument table 102 by means of several similar instrument connectors C, and the dental device is arranged to identify the instrument used at a given time. In response to this, the electronics unit 108 adjusts physical variables according to each instrument. Electric wires, signal wires and pipes needed for conveying water and air travel inside the cable conduit 106.

Controllers functionally connected to the dental device, such as a keyboard 116 and a foot control 117, are used to transmit control commands to the electronics unit 110 of the frame part of the dental device and/or directly to the electronics unit 108 of the instrument table. These control commands can adjust the operation and settings of the instruments. The electronics units may include a digital data processing unit, such as a microprocessor, to which control information formed is transmitted from the controller 116, 117 preferably by means of a control signal.

To solve the above-mentioned hygiene problems, the controller 116 is preferably implemented as a touch pad, which in cooperation with the graphic display is arranged to produce control information, preferably a control signal, for the dental device in response to the fact that the controller's touch pad is pointed at with a pointer means, such as a pointer pen or a finger. In this application, the 'touch pad' refers to a user interface which is sensitive to touch and movement and used for feeding control information into the dental device. The user feeds control information, such as a command, into the dental device by moving and touching or pressing a touch-sensitive area of the touch pad, i.e. the contact surface, e.g. by a finger or another pointer means. The touch pad can be used in the same way as a mouse controller by moving the pointer means on the contact surface. In dental treatments, it is advantageous to use touch pads as the control means of the dental device since touch pads are easy to clean and disinfect thanks to their materials and simple shape.

According to a preferred embodiment of the invention, feeding control information by means of the touch pad requires pressing of the contact surface. Touch pads that require pressing typically comprise several material layers which are separated from one another and arranged to form an electrode network where electric current flows. When the user presses the contact surface, the material layers touch one another at the point pressed, in which case the current flow is interrupted in the electrode network. The point pressed in the touch pad can be determined by a 'detection circuit', which is arranged to detect an interruption in the current flow.

One touch pad suitable for use in the invention is, for example, a touch pad which comprises a resistive or capacitive contact surface and can detect both a movement and a press. The surface of a resistive touch pad is coated with a thin conductive and resistive layer. On top of the touch-sensitive area of the capacitive touch pad, there is a layer which forms a pixel-like capacitor matrix and whose electric properties change as a finger touches the surface since the capacitance of human body connects part of the voltage of the contact point to the earth. The contact point of the touch pad can be determined by measuring the resistance or capacitance values of the touch pad surface. An advantage of the capacitive contact surface is that it also functions well when touched with resistive protective gloves, which may constitute a problem in the case of a resistive contact surface.

According to a preferred embodiment of the invention, the contact surface of the touch pad is implemented so that it sustains chemical disinfection. Exposition of the surface to disinfectant can preferably be reduced by attaching a thin, detachable and preferably disinfectable or disposable film to the contact surface. A touch can be detected through the film, which can be replaced by a new one after it has worn out.

The touch pad can also be connected to the dental device through an interface. Thus the touch pad itself can be placed onto another surface of the dental device, for example integrated into the top of the instrument table. Correspondingly, the touch pad may be arranged in the patient chair, for example under the backrest. In addition, according to the invention, the touch pad can be implemented as a separate auxiliary device, which can be mechanically attached by an arm to a dental table or to another object, such as a cabinet in the treatment room. The touch pad may also be provided with a support of its own, in which case its location in relation to the dental device can be changed freely. In the placement of the touch pad, attention can also be paid to ergonomics by placing the touch pad within reach close to the subject, for instance. In particular, the invention enables free placement of the user interface so that the user of the dental device does not need to see which key his finger touches, for example. Consequently, the touch pad can be placed ergonomically or otherwise appropriately.

Figure 2:
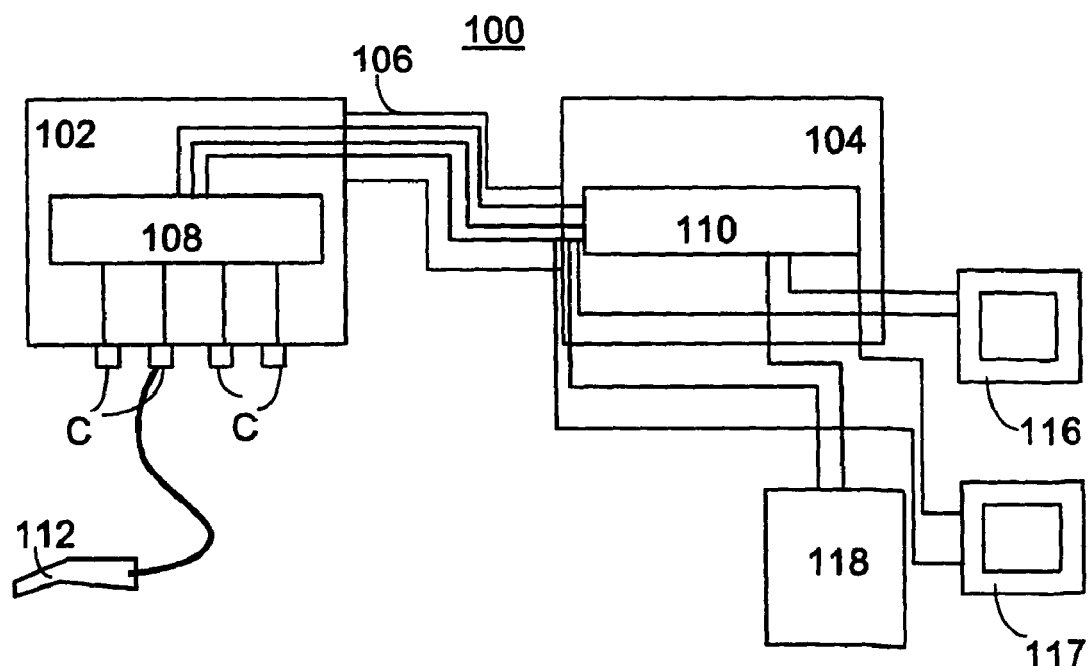
FIG. 2 is a block diagram illustrating a dental apparatus according to a preferred embodiment of the invention.

FIG. 2 illustrates a dental apparatus according to a preferred embodiment of the invention, which in accordance with FIG. 1 comprises a dental device and a control apparatus connected functionally to it. In addition, a graphic display 118 is functionally connected to the dental apparatus. The graphic display in the dental device may show information on the patient, on the operations to be performed/that have been performed on him and on the patient's health. Furthermore, by means of the touch pad, the dental device can be controlled through a computer by utilizing patient information in controlling the dental device. In that case, the computer can be controlled to transmit, for example, a control signal for adjusting the patient chair to a position suitable for the anatomy of a patient who has visited the clinic earlier or to set operating parameters for the instruments according to the operation to be performed.

It will be obvious to a person skilled in the art that as the technology advances, the inventive concept can be implemented in various ways. The invention and its embodiments are thus not restricted to the above examples but they may vary within the scope of the claims.

The invention claimed is:

1. Dental apparatus, comprising:
   a dental device;
   a graphic display functionally connected to said dental device, said graphic display structured and arranged to display symbols on a screen thereof identifying respective control functions of said dental device, said graphic display further structured and arranged to display a cursor on said screen thereof, said cursor being movable to positions on said screen in relation to said symbols for selecting and activating a control function of said dental device; and
   a touch pad including a contact surface for detecting both movement thereon and pressing thereof by a pointer means, said touch pad functionally connected to said dental device and graphic display and structured and arranged for selecting a respective control function of said dental device represented by a respective symbol by moving said cursor in relation to said symbols by movement of the pointer means on said contact surface of said touch pad and for then activating said selected control function of said dental device by pressing of said contact surface of said touch pad by the pointer means; and wherein;
   said graphic display and said touch pad are structured and arranged separately from each other such that said graphic display and touch pad can be situated relative to said dental device independently of each other.

2. A dental apparatus according to claim 1, wherein the functional connection between the touch pad and the graphic display is arranged through a computer.

3. A dental apparatus according to claim 2 wherein the touch pad is arranged to control the computer functionally connected to the dental device.

4. A dental apparatus according to claim 2 wherein the touch pad is arranged to control the dental device through the computer.

5. A dental apparatus according to claim 2 wherein the touch pad is arranged to form control information for the dental device through the computer so that the control information is modified on the basis of patient information included in the computer.

6. A dental apparatus according to claim 1 wherein the pointer means is a pointer pen or a finger.

7. A dental apparatus according to claim 1, wherein the touch pad comprises a capacitive or a resistive contact surface.

8. A dental apparatus according to claim 7, wherein the touch pad is arranged to form control information for the dental device in response to the fact that the contact surface of the touch pad is pressed or something slides on it so that material layers included in the touch pad touch one another at a point in question, in which case a current flow is interrupted in an electrode network included in the touch pad.

9. A dental apparatus according to claim 7, wherein a detachable and disinfectable or disposable film is arranged to be attached to the contact surface.

10. A dental apparatus according to claim 1, wherein the touch pad is integrated into the dental device or is arranged to be placed under a backrest of a patient chair included in the dental apparatus.

* * * * *